(12) United States Patent
Balthasart

(10) Patent No.: US 6,677,467 B2
(45) Date of Patent: Jan. 13, 2004

(54) OXIRANE PRODUCTION USING PEROXIDIZED COMPOUND

(75) Inventor: Dominique Balthasart, Brussels (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 10/311,308

(22) PCT Filed: Jun. 26, 2001

(86) PCT No.: PCT/EP01/07273

§ 371 (c)(1),
(2), (4) Date: Dec. 27, 2002

(87) PCT Pub. No.: WO02/00637

PCT Pub. Date: Jan. 3, 2002

(65) Prior Publication Data

US 2003/0109726 A1 Jun. 12, 2003

(30) Foreign Application Priority Data

Jun. 28, 2000 (FR) ............................................ 00 08355

(51) Int. Cl.⁷ ...................... C07D 301/12; C07D 301/19
(52) U.S. Cl. ........................................ 549/531; 549/529
(58) Field of Search .................................. 549/531, 529

(56) References Cited

U.S. PATENT DOCUMENTS 5,849,937 A    12/1998   Jubin, Jr.

FOREIGN PATENT DOCUMENTS

| EP | 0 659 473 | 6/1995 |
| WO | 99/24164 | 5/1999 |
| WO | 99/28029 | 6/1999 |
| WO | 99/48882 | 9/1999 |
| WO | 99/48883 | 9/1999 |
| WO | 00/31057 | 6/2000 |

*Primary Examiner*—Ba K. Trinh
(74) *Attorney, Agent, or Firm*—Oblon, Spivak, McClelland, Maier & Neustadt, P.C.

(57) ABSTRACT

Process for manufacturing oxirane by reaction of an olefin with a peroxide compound in the presence of a catalyst and a solvent in at least two reactors arranged in series, each of which contains a portion of catalyst, according to which the peroxide compound is introduced only into the first reactor, the subsequent reactor(s) not being fed with fresh peroxide compound, but only with the peroxide compound which is present in the medium obtained from the preceding reactor and which was not consumed in this preceding reactor.

10 Claims, 1 Drawing Sheet

OXIRANE PRODUCTION USING PEROXIDIZED COMPOUND

Figure 1:
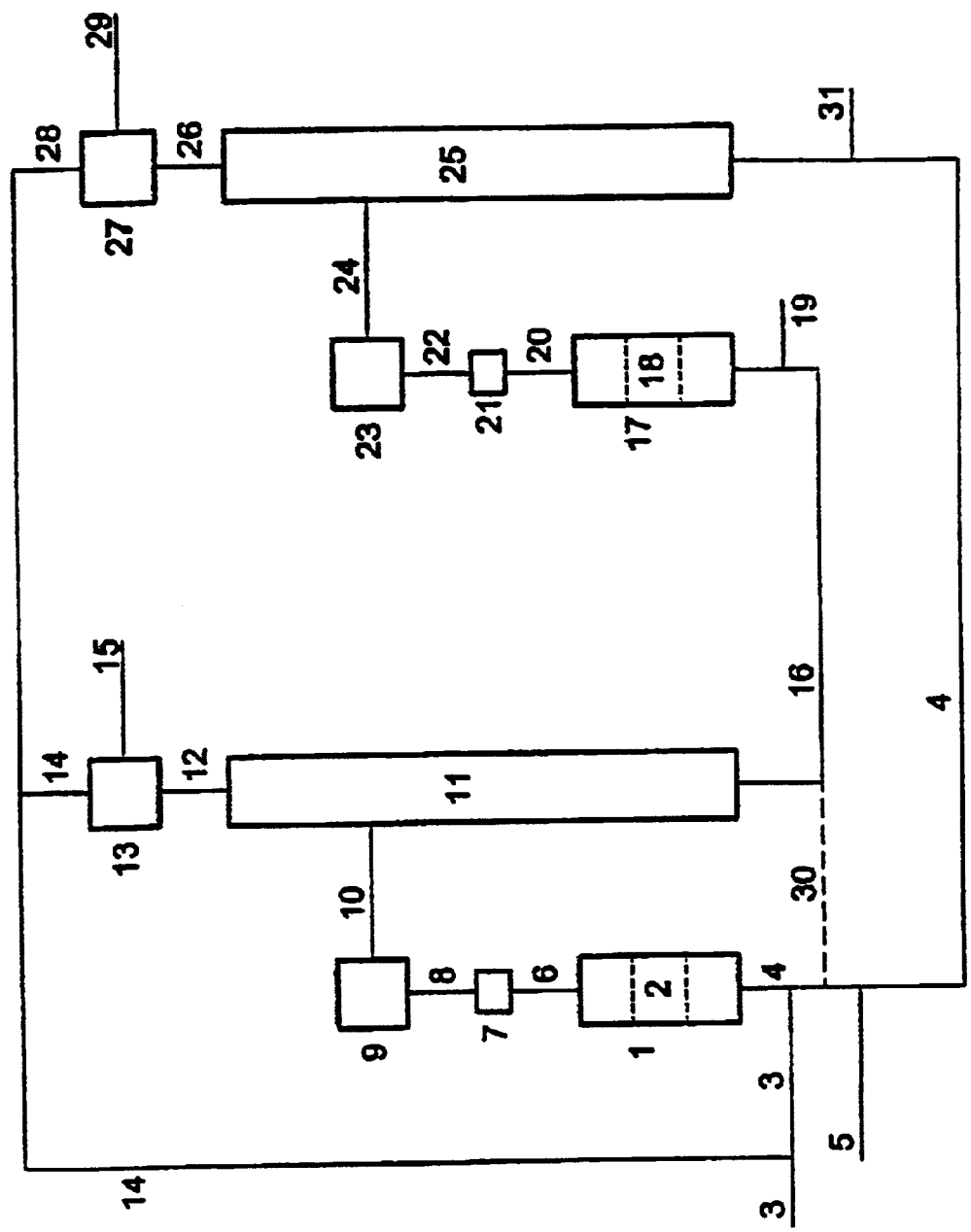

This application is a 371 of PCT/EP01/07273 filed Jun. 26, 2001.

The present invention relates to a process for manufacturing oxirane by reaction between an olefin and a peroxide compound in the presence of a catalyst and a solvent. In particular, the invention relates to the manufacture of propylene oxide (or epichlorohydrin) by epoxidation of propylene (or allyl chloride) using hydrogen peroxide in the presence of a catalyst containing TS-1.

It is known practice to manufacture propylene oxide by reaction between propylene and hydrogen peroxide in the presence of TS-1. For example, in patent U.S. Pat. No. 5,849,937, such a process is performed in several reactors arranged in series. In this known process, each reactor of the series is fed with fresh hydrogen peroxide.

The Applicant has found that when each reactor is fed with fresh hydrogen peroxide, it is impossible to convert the entire amount of hydrogen peroxide used without substantial formation of by-products and thus impossible to have an optimum yield.

The present invention overcomes this drawback by providing a novel process which makes it possible to convert 100% of the amount of hydrogen peroxide introduced, with a low formation of by-products and without, however, reducing the reaction rate.

To this end, the invention relates to a process for manufacturing oxirane by reaction of an olefin with a peroxide compound in the presence of a catalyst and a solvent in at least two reactors arranged in series, each of which contains a portion of catalyst, according to which a first portion of the olefin, the solvent and all of the peroxide compound are introduced into a first reactor, an epoxidation of the first portion of the olefin is carried out therein in order to form a first portion of the oxirane, a medium comprising the first portion of the oxirane formed, the solvent, the unconsumed peroxide compound and possibly the unconverted olefin is removed from this reactor, the medium and another portion of the olefin are introduced into a subsequent reactor, an epoxidation of the other portion of the olefin is carried out therein using the unconsumed peroxide compound obtained from the first reactor, in order to form another portion of the oxirane, and the other portion of the oxirane thus formed is collected.

One of the essential characteristics of the present invention lies in the fact that the peroxide compound is only introduced into the first reactor. The subsequent reactor(s) is (are) thus not fed with fresh peroxide compound, but only with the peroxide compound which is present in the medium obtained from the preceding reactor and which has not been consumed in this preceding reactor. In general, water is also introduced with the peroxide compound into the first reactor. The fact that no peroxide compound is added to the subsequent reactor(s) makes it possible to consume 100% of the total amount of peroxide compound used without, however, reducing the reaction rate when compared with a process using the same total amount of peroxide compound, but in which each reactor is fed with fresh peroxide compound.

In the process according to the invention, a plant comprising at least two epoxidation reactors arranged in series and connected together is used. Each reactor is fed with olefin. The peroxide compound and the solvent are only introduced into the first reactor. Each reactor contains a portion of the catalyst which does not leave that reactor. When the catalyst is present in the form of a fixed bed, it is generally not necessary to take precautions to keep the catalyst in the reactor. Alternatively, the catalyst may be present in the form of particles, at least some of which are in a form fluidized by a liquid stream or by mechanical stirring or by a gas. When a liquid stream is used, it is recommended to include a fall-out zone above the fluid bed to stop the catalyst particles which are in motion and/or to include a filter at the reactor outlet.

Needless to say, the plant may comprise more than two reactors connected in series. In this case, the first reactor of the series is fed with the olefin, the peroxide compound and the solvent and each subsequent reactor is fed with the olefin and the medium obtained from the preceding reactor of the series. Preferably, 3 reactors in series are used.

In the process according to the invention, at least 50% of the total amount of peroxide compound used in the first reactor is generally consumed in the first reactor. The best yields are obtained when at least 70% are consumed in the first reactor. Usually, not more than 99% are consumed in the first reactor, and preferably not more than 85%. The remainder is consumed in the subsequent reactor(s).

In the process according to the invention, reactors of identical size are preferably used. This makes it possible to interchange the function of the reactors when the deactivated catalyst in one reactor is replaced with fresh or regenerated catalyst without disrupting the functioning of the plant (so-called "carousel" functioning).

A first embodiment of the process according to the invention consists in using the catalyst in the form of particles, at least some of which are in fluidized form, as disclosed in the Applicant's patent application filed on the same day as the present patent application and entitled "Process for manufacturing oxirane in the presence of a catalyst in the form of particles" (the content of which is incorporated by reference). In this case, it is recommended to include a filter through which the medium leaving the first reactor passes before being introduced into the subsequent reactor. This embodiment makes it possible to obtain a homogeneous dispersion of the catalyst in the epoxidation reaction medium, good heat exchange and thus easy control of the reaction temperature.

In a second embodiment of the process according to the invention, the medium entering the subsequent reactor is first subjected to a depressurization before being introduced into the subsequent reactor. This embodiment is particularly suitable when the epoxidation is carried out under pressure or in the presence of a gaseous compound. This gaseous compound may be the olefin itself (for example propylene) or an inert gas which is introduced into the epoxidation reaction medium to allow the oxirane to be entrained and removed from the reactor, as disclosed in patent application WO 99/48883 by the Applicant.

In a third embodiment of the process according to the invention, the medium entering the subsequent reactor is first subjected to a treatment to separate out the oxirane formed before being introduced into the subsequent reactor. The aim of this embodiment is to separate the oxirane from the epoxidation reaction medium as quickly as possible after it is formed in order to prevent the formation of by-products by hydrolysis or alcoholysis (methanolysis when methanol is used as solvent) of the oxirane formed. This embodiment thus has the advantage of leading to a high selectivity. The separation treatment is preferably a distillation, as disclosed in the Applicant's patent application filed on the same day as the present patent application and entitled "Process for manufacturing oxirane comprising the separation of the oxirane from the reaction medium" (the content of which is incorporated by reference).

One preferred embodiment of the process according to the invention is represented schematically in FIG. 1. In this preferred embodiment, the first reactor 1 contains a portion of the catalyst, preferably as a fluid bed 2. The reactor 1 is fed with a first portion of the olefin via pipe 3 and then via pipe 4, with peroxide compound via pipe 5 and then via pipe 4, and with solvent via pipe 4 obtained from another part of the plant which is described later. In the first reactor, the first portion of the olefin reacts with the peroxide compound in the presence of the catalyst to form a first portion of the oxirane. The medium leaving reactor 1 via pipe 6 contains the solvent, the first portion of the oxirane, the unconsumed peroxide compound and the unconverted olefin. This medium passes through a filter 7 and is conveyed via pipe 8 into the container 9, in which it undergoes a depressurization. The medium is then conveyed via pipe 10 into a distillation column 11. A mixture of oxirane and of unconverted olefin is recovered at the top of this distillation column 11. This mixture is conveyed via pipe 12 into a condenser 13 which separates the oxirane from the unconverted olefin. The unconverted olefin is recycled into reactor 1 via pipes 14, 3 and 4. The first portion of oxirane is collected as finished product via pipe 15. A medium containing the solvent, the peroxide compound not consumed in reactor 1 and possibly some of the unconverted olefin is collected at the bottom of the distillation column 11. This medium, a portion of which may optionally be recycled into the reactor 1 via pipe 30, is transported via pipe 16 into a second reactor 17 containing another portion of the catalyst, preferably in the form of a fluid bed 18. The second reactor 17 is fed with a second portion of the olefin via pipe 19. In the second reactor 17, the second portion of the olefin reacts with the unconsumed peroxide compound obtained from the first reactor in the presence of catalyst 18 to form a second portion of the oxirane. The conditions in the second reactor 17 are preferably such that all of the peroxide compound obtained from the first reactor is consumed. The medium leaving reactor 17 via pipe 20 thus contains the solvent, the second portion of the oxirane and the unconverted olefin. This medium passes through a filter 21 and is conveyed via pipe 22 into the container 23, in which it undergoes a depressurization. The medium is then transported via pipe 24 into a second distillation column 25. A mixture of the second portion of oxirane and of unconverted olefin is recovered at the top of this distillation column 25. This mixture is conveyed via pipe 26 into a condenser 27 which separates the oxirane from the unconverted olefin. The unconverted olefin is recycled into the reactor 1 via pipes 28, 14, 3 and 4. The second portion of oxirane is collected as finished product via pipe 29. The solvent, which is collected at the bottom of the distillation column 25, and is recycled via pipe 4 into the first reactor 1.

The catalyst used in the process according to the invention generally contains a zeolite as active element, and preferably a titanium zeolite. The term "titanium zeolite" is intended to denote a solid containing silica which has a microporous crystal structure of zeolite type and in which several silicon atoms are replaced with titanium atoms. The titanium zeolite advantageously has a crystal structure of ZSM-5, ZSM-11, ZSM-12, MCM-41 or ZSM-48 type. It may also have a crystal structure of beta zeolite type, preferably free of aluminium. Zeolites with an infrared absorption band at about 950–960 cm$^{-1}$ are suitable for use. Titanium zeolites of silicalite type are preferred. Those corresponding to the formula $xTiO_2(1-x)SiO_2$ in which x is from 0.0001 to 0.5 and preferably from 0.001 to 0.05 give high-quality performance. Materials of this type, known under the name TS-1, have a microporous crystalline zeolite structure similar to that of the zeolite ZSM-5.

The catalyst used in the process according to the invention is advantageously in the form of particles obtained by extrusion as disclosed in patent application WO 99/28029 by the Applicant, or by a spray process as disclosed in patent application WO 99/24164 by the Applicant. The content of these two patent applications is incorporated herein by reference.

The solvent used in the process according to the invention may be chosen from linear or branched saturated aliphatic alcohols. The alcoholic solvent generally contains up to 10 carbon atoms and preferably from 1 to 6 carbon atoms. Examples which may be mentioned are methanol and ethanol. Methanol is preferred.

The amount of solvent used in the first reactor is generally at least 25% by weight of the liquid reaction medium present in the first reactor, in particular at least 40% by weight, for example at least 50% by weight. This amount usually does not exceed 99% by weight and in particular does not exceed 95% by weight.

The molar ratio between the amounts of olefin and of peroxide compound that are used in the process according to the invention is generally at least 0.1, in particular at least 0.2 and preferably at least 0.5. This molar ratio is usually not more than 100, in particular not more than 50 and preferably not more than 25.

The process according to the invention may be continuous or batchwise.

In the process according to the invention, when it is performed continuously, the peroxide compound is generally used in the first reactor in an amount of at least 0.005 mol per hour and per gram of catalyst present in the first reactor, in particular at least 0.01 mol. The amount of peroxide compound is usually less than or equal to 25 mol and in particular less than or equal to 10 mol. Preference is shown for an amount of peroxide compound of greater than or equal to 0.03 mol and less than or equal to 2.5 mol.

In the process according to the invention, the peroxide compound is advantageously used in the form of an aqueous solution. In general, the aqueous solution contains at least 2% by weight of peroxide compound and in particular at least 5% by weight. It usually contains not more than 90% by weight of peroxide compound and in particular not more than 70% by weight.

The temperature of the reaction between the olefin and the peroxide compound may range from 10° C. to 125° C. In one advantageous variant as disclosed in patent application EP 99/08703 by the Applicant, it is greater than 35° C. in order to overcome the gradual deactivation of the catalyst. The temperature may be greater than or equal to 40° C. and preferably greater than or equal to 45° C. A temperature of greater than or equal to 50° C. is most particularly preferred. The reaction temperature is preferably less than 100° C.

In the process according to the invention, the reaction between the olefin and the peroxide compound may take place at atmospheric pressure. It may also take place under pressure. This pressure generally does not exceed 40 bar. A pressure of 20 bar is suitable in practice.

The peroxide compounds which may be used in the process according to the invention are peroxide compounds containing one or more peroxide functions (—OOH) which may release active oxygen and which are capable of carrying out an epoxidation. Hydrogen peroxide and peroxide compounds which may produce hydrogen peroxide under the conditions of the epoxidation reaction are suitable for use. Hydrogen peroxide is preferred.

When hydrogen peroxide is used, it may be advantageous to use, in the process according to the invention, an aqueous hydrogen peroxide solution in crude form, i.e. in unpurified form. For example, a solution obtained by simple extraction, with substantially pure water, of the mixture obtained from the oxidation of at least one alkylanthrahydroquinone (process known as "autoxidation AO process") may be carried out, without a subsequent washing and/or purification treatment. These crude hydrogen peroxide solutions generally contain from 0.001 to 10 g/l of organic impurities expressed as TOC (Total Organic Carbon). They usually contain metal cations (such as alkali metals or alkaline-earth metals, for instance sodium) and anions (such as phosphates or nitrates) in contents of from 0.01 to 10 g/l.

In another variant of the process, a hydrogen peroxide solution produced by direct synthesis from oxygen and hydrogen in the presence of methanol may be used.

The oxirane which may be prepared by the process according to the invention is an organic compound comprising a group corresponding to the general formula:

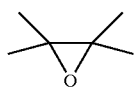

The oxirane generally contains from 2 to 10 carbon atoms and preferably from 3 to 6 carbon atoms. The oxiranes which may be prepared advantageously by the process according to the invention are 1,2-epoxypropane and 1,2-epoxy-3-chloropropane. The preferred oxirane is 1,2-epoxypropane.

The olefins which are suitable for use in the process according to the invention generally contain from 2 to 10 carbon atoms and preferably from 3 to 6 carbon atoms. Propylene, butylene and allyl chloride are suitable for use. Propylene and allyl chloride are preferred. Propylene is most particularly preferred.

In the process according to the invention, it may prove to be advantageous to monitor the pH of the liquid phase. For example, it may be advantageous to maintain the pH of the liquid phase during the reaction between the olefin and the peroxide compound at a value of from 4.8 to 6.5, for example by adding a base (sodium hydroxide) to the epoxidation medium, as recommended in patent application WO 99/48882 by the Applicant (the content of which is incorporated into the present patent application by reference). This base may be introduced into only one reactor (for example the first reactor) or into several reactors. It is preferably introduced into each reactor.

The reaction between the olefin and the peroxide compound may be carried out in the presence of a salt such as sodium chloride, as disclosed in patent application WO EP 99/08703 by the Applicant (the content of which is incorporated by reference into the present patent application). This salt may be introduced into only one reactor (for example the first reactor) or into several reactors. It is preferably introduced into each reactor.

It may be advantageous to introduce the olefin in a form diluted in one or more alkanes. For example, a fluid containing the olefin and also at least 10% (in particular 20%, for example at least 30%) by volume of one or more alkanes may be introduced into the epoxidation reactors. For example, in the case of propylene, the latter may be mixed with at least 10% by volume of propane when the recycled unconverted propylene is introduced into the reactor. It may also be a source of propylene which is not completely freed of propane.

What is claimed is:

1. A process for manufacturing oxirane by reaction of an olefin with a peroxide compound in the presence of a catalyst and a solvent in at least two reactors arranged in series, each of which contains a portion of catalyst, according to which a first portion of the olefin, the solvent and all of the peroxide compound are introduced into a first reactor, an epoxidation of the first portion of the olefin is carried out therein in order to form a first portion of the oxirane, a medium comprising the first portion of the oxirane formed, the solvent, the unconsumed peroxide compound and possibly the unconverted olefin is removed from this reactor, the medium and another portion of the olefin are introduced into a subsequent reactor, an epoxidation of the other portion of the olefin is carried out therein using the unconsumed peroxide compound obtained from the first reactor, in order to form another portion of the oxirane, and the other portion of the oxirane thus formed is collected.

2. The process according to claim 1, in which 50% to 99% of the total amount of peroxide compound used in the first reactor is consumed in the first reactor, the remainder being consumed in the subsequent reactor(s).

3. The process according to claim 1, in which all the reactors are of identical size.

4. The process according to claim 1, in which the catalyst is present in each reactor in the form of particles, at least some of which are in fluidized form.

5. The process according to claim 4, in which the medium leaving the first reactor passes through a filter before being introduced into the subsequent reactor.

6. The process according to claim 1, in which the medium entering the subsequent reactor is first subjected to a depressurization before being introduced into the subsequent reactor.

7. The process according to claim 1, in which the medium entering the subsequent reactor is first subjected to a treatment to separate out the oxirane formed before being introduced into the subsequent reactor.

8. The process according to claim 7, in which the separation treatment is a distillation.

9. The process according to claim 1, in which the oxirane is epichlorohydrin, the olefin is allyl chloride, the peroxide compound is hydrogen peroxide, the solvent is methanol and the catalyst contains TS-1.

10. The process according to claim 1, in which the oxirane is propylene oxide, the olefin is propylene, the peroxide compound is hydrogen peroxide, the solvent is methanol and the catalyst contains TS-1.

* * * * *

UNITED STATES PATENT AND TRADEMARK OFFICE
CERTIFICATE OF CORRECTION

PATENT NO. : 6,677,467 B2
DATED : January 13, 2004
INVENTOR(S) : Dominique Balthasart It is certified that error appears in the above-identified patent and that said Letters Patent is hereby corrected as shown below:

Column 1,
Line 63, "and connected together is used." should read -- and connected together, with the exception of at least two successive reaction zones arranged in a single reactor. These reactors are therefore separate reactors.--

Column 3,
Line 53, "via pipe 4 into the first reactor 1." should read -- via pipe 4 into the first reactor 1, and an aqueous effluent which is discharged via pipe 31. --

Column 4,
Line 64, "out an epoxidation." should read -- out an epoxidation. Inorganic peroxide compounds give good results. --

Column 6,
Line 8, insert the following paragraphs:
-- The examples that follow are intended to illustrate the present invention without, however, limiting its scope.
Examples 1 and 2 were calculated using the ASPEN PLUS® program from the company ASPEN TECHNOLOGY INC. with the aid of the kinetic parameters of the reaction determined on the basis of the experimental tests described and the liquid-vapour equilibria available in the literature.

Comparative Example 1

In this example, the synthesis of propylene oxide is performed in two reactors in series with intermediate separation of the propylene oxide formed in the first reactor in a rectification column. Half the $H_2O_2$ is fed into the first reactor, and half into the second reactor.
326.5 kmol/h of hydrogen peroxide accompanied by 1 100 kmol/h of water are divided into two equal fractions each containing 163.25 kmol/h of hydrogen peroxide and 550 kmol/h of water; the first fraction is mixed with 1 500 kmol/h of methanol, 250 kmol/h of propylene and the fraction recycled from the bottom of the rectification column under a pressure sufficient to dissolve all the propylene at the reaction temperature. The reaction mixture is introduced continuously at 70°C into a methodic reactor containing 600 kg of catalyst. The reactor is maintained at 70°C by means of an adequate cooling system.

UNITED STATES PATENT AND TRADEMARK OFFICE
CERTIFICATE OF CORRECTION

PATENT NO. : 6,677,467 B2
DATED : January 13, 2004
INVENTOR(S) : Dominique Balthasart It is certified that error appears in the above-identified patent and that said Letters Patent is hereby corrected as shown below:

Column 6, (cont)
The reactor effluent is conveyed to a rectification column containing 50 theoretical plates (including condenser and boiler); the feed is effected into the 10th theoretical plate (starting from the condenser); the column is run at 1.1 bar absolute (column head pressure); the column head temperature is maintained at 40°C (distillate partially vapourized); the degree of molar reflux is set at 1; the total flow rate of distillate is set at 600 kmol/h.
The mixture withdrawn, from the bottom of the column, which is depleted in propylene oxide, is divided into two fractions, the first, containing 90 volt of the mixture, is recycled into the first reactor feed; the second, which contains the remainder of the mixture obtained from the bottom of the rectification column, is mixed with 200 kmol/h of propylene at a pressure sufficient to fully dissolve the propylene at the reaction temperature, and is introduced continuously at 70°C into a second methodic reactor containing 820 kg of catalyst and maintained at 70°C by means of an adequate cooling system.
The effluent from the second reactor contains 24.5 kmol/h of unreacted hydrogen peroxide, 209.4 kmol/h of propylene oxide and 87.7 kmol/h of by-products (mainly methoxypropanol and propanediol); the column distillate contains 56.2 kmol/h of propylene oxide; the yield of C3 is up to 64.1% for a degree of conversion of the hydrogen peroxide of 92.4%.
Example 2 (in accordance with the invention)

In this example, the synthesis of propylene oxide is performed in 2 reactors in series with intermediate separation of the propylene oxide formed in the first reactor.
326.5 kmol/h of hydrogen peroxide accompanied by 1 100 kmol/h of water are mixed with 1 500 kmol/h of methanol, with 250 kmol/h of propylene and with the fraction recycled from the bottom of the rectification column under a pressure sufficient to dissolve all the propylene at the reaction temperature. The reaction mixture is introduced continuously at 70°C into a methodic reactor containing 600 kg of catalyst. The reactor is maintained at 70°C by means of an adequate cooling system.
The reactor effluent is conveyed to a rectification column containing 50 theoretical plates (including condenser and boiler); the feed is effected into the 10th theoretical plate (starting from the condenser); the column is run at 1.1 bar absolute (column head pressure); the column head temperature is maintained at 40°C (distillate partially vapourized); the degree of molar reflux is set at 1; the total flow rate of distillate is set at 600 kmol/h.
The mixture withdrawn from the bottom of the column, which is depleted in propylene oxide, is divided into two fractions, the first, containing 90 volt of the mixture, is recycled into the first reactor feed; the second, containing the remainder of the mixture obtained from the bottom of the rectification column, is mixed with 200 kmol/h of propylene at a pressure sufficient to fully dissolve the propylene at the reaction temperature, and is introduced continuously at 70°C into a second methodic reactor containing

UNITED STATES PATENT AND TRADEMARK OFFICE
CERTIFICATE OF CORRECTION

PATENT NO. : 6,677,467 B2
DATED : January 13, 2004
INVENTOR(S) : Dominique Balthasart It is certified that error appears in the above-identified patent and that said Letters Patent is hereby corrected as shown below:

<u>Column 6, (cont)</u>
820 kg of catalyst and maintained at 70°C by means of an adequate cooling system.
 The effluent from the second reactor contains 1.9 kmol/h of unconverted hydrogen peroxide, 256.5 kmol/h of propylene oxide and 62.2 kmol/h of by-products (mainly methoxypropanol and propanediol); the column distillate contains 88.4 kmol/h of propylene oxide; the yield of C3 is up to 78.6% for a degree of conversion of the hydrogen peroxide of 99.4%. --

Signed and Sealed this

First Day of March, 2005

JON W. DUDAS
*Director of the United States Patent and Trademark Office*